United States Patent
Fan et al.

(10) Patent No.: US 8,137,275 B2
(45) Date of Patent: Mar. 20, 2012

(54) TISSUE COMPLEX MODULUS AND/OR VISCOSITY ULTRASOUND IMAGING

(75) Inventors: Liexiang Fan, Sammamish, WA (US); Paul Freiburger, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1300 days.

(21) Appl. No.: 11/824,388

(22) Filed: Jun. 28, 2007

(65) Prior Publication Data
US 2009/0005682 A1    Jan. 1, 2009

(51) Int. Cl.
*A61B 8/00* (2006.01)
(52) U.S. Cl. ...................................................... 600/438
(58) Field of Classification Search .................. 600/438
See application file for complete search history.

(56) References Cited

U.S. PATENT DOCUMENTS

| | | | |
|---|---|---|---|
| 5,107,837 A | 4/1992 | Ophir et al. | |
| 5,178,147 A | 1/1993 | Ophir et al. | |
| 5,293,870 A | 3/1994 | Ophir et al. | |
| 5,474,070 A * | 12/1995 | Ophir et al. | 600/437 |
| 5,810,731 A | 9/1998 | Sarvazyan et al. | |
| 6,508,768 B1 | 1/2003 | Hall et al. | |
| 6,558,324 B1 | 5/2003 | Von Behren et al. | |
| 6,682,485 B2 * | 1/2004 | Seitz et al. | 600/438 |
| 6,770,033 B1 | 8/2004 | Fink et al. | |
| 6,951,544 B2 | 10/2005 | Trahey et al. | |
| 2005/0004463 A1 | 1/2005 | Chen et al. | |
| 2005/0252295 A1 | 11/2005 | Fink et al. | |

OTHER PUBLICATIONS

G. Zhang, "Evaluating the viscoelastic properties of biological tissues in a new way", J. of Musculoskeletal Neuronal Interact, 2005, 5(1), pp. 85-90.
L. Nielsen, et al., "Improved Method for Complex Modulus Estimation", Application Note—Bruel & Kjaer, 1996, pp. 1-8.

* cited by examiner

*Primary Examiner* — Jonathan Cwern

(57) ABSTRACT

Complex response of tissue is calculated as function of a convolution relationship associated with measured strain with applied stress. In the Fourier or frequency domain, the convolution is a simple algebraic computation, such as multiplication. The complex response provides elasticity and viscosity information, assisting diagnosis. Complex compliance may be directly calculated from the strain and stress. Complex fluidity may be directly calculated from strain rate and stress.

12 Claims, 2 Drawing Sheets

US 8,137,275 B2

TISSUE COMPLEX MODULUS AND/OR VISCOSITY ULTRASOUND IMAGING

BACKGROUND

The present embodiments relates to tissue property ultrasound imaging. Tissue is a viscoelastic material. Changes in tissue on a molecular level may be identified by the viscoelasticity.

One tissue property or component of viscoelasticity is elasticity. Ultrasound imaging may operate in an elasticity imaging mode. U.S. Pat. Nos. 5,107,837, 5,293,870, 5,178,147, and 6,508,768 describe methods to generate elasticity images using the relative tissue displacement between adjacent frames. The tissue strain is determined in response to a stress applied to tissue. The stress is applied externally, such as by manual pressure or by acoustic pressure. Strain, strain rate, modulus (e.g., hardness), or other parameters corresponding to tissue displacement are detected for generating an elasticity image. U.S. Pat. No. 6,558,324 describes methods to represent elasticity using color coding.

Similarly, shear velocity and relaxation time of tissue under stress may be determined. Altered stiffness regions may be identified.

BRIEF SUMMARY

By way of introduction, the preferred embodiments described below include methods, instructions, and systems for determining viscoelastic tissue property. Complex response of tissue is calculated as function of a convolution relationship associated with measured strain with applied stress. In the Fourier or frequency domain, the convolution is a simple algebraic computation, such as multiplication. The complex response provides elasticity and viscosity information, assisting diagnosis. Complex compliance may be calculated from strain and stress. Complex fluidity may be calculated from strain rate and stress.

In a first aspect, a method is provided for determining viscoelastic tissue property. An applied stress is determined. Tissue strain in response to the applied stress is measured with ultrasound. A complex tissue property is determined from a convolution relationship.

In a second aspect, a computer readable storage medium has stored therein data representing instructions executable by a programmed processor for determining viscoelastic tissue property. The storage medium includes instructions for determining tissue displacement as a function of time, the tissue displacement being responsive to a stress, the determining being from received ultrasound information, and calculating a complex modulus, complex compliance, complex viscosity, complex fluidity, or combinations thereof as a function of the tissue displacement and the stress.

In a third aspect, a system is provided for determining viscoelastic tissue property. A transducer is operable to generate receive signals from received ultrasound energy. A receive beamformer is operable to output data representing spatial locations along at least a line. An image processor is operable to: determine strain or strain rate as a function of the output data, transform the strain or strain rate into a frequency domain, and calculate elasticity and viscosity tissue properties by algebraic function in the frequency domain.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Strain response can be represented by the convolution of stress and tissue's complex compliance (or the inverse complex modulus). The strain rate can be represented by the convolution of tissue's complex fluidity (or the inverse complex viscosity) and stress. A stress input is known or may be estimated. The deformation of tissue may be measured as displacement with ultrasound. The strain or strain rate may be determined for a given stress. By applying a Fourier transform to the stress and strain or strain rate, the complex compliance or fluidity may be estimated using algebraic functions. The reciprocal complex modulus and complex viscosity may be estimated. Rather than just elasticity, a complex representation is estimated.

The complex tissue properties may include elasticity and viscosity. These properties may be useful in diagnosis, such as diagnosing tissue type and or pathology. Many applications are possible, such as evaluating liver fibrosis, characterizing breast lesions, monitoring ablation progress, classifying plaque or blockages, or other applications.

Tissue viscoelasticity includes both viscosity and elasticity components. Each component has a complex response—real and imaginary response. The elasticity represents the complex compliance or the inverse complex modulus. The viscosity represents the complex fluidity or the inverse complex viscosity. The fluidity and viscosity relate to the strain rate, and the compliance and modulus relate to the strain. Strain rate is the time derivative of the strain. Mean or other values for elasticity and viscosity may be determined from the complex information.

The strain may be represented as $\epsilon(t)$ and strain rate as $\dot{\epsilon}(t)$. For polymeric material, the strain and strain rate may be related to stress, $\sigma(t)$, by:

$$\epsilon(t) = c(t) \otimes \sigma(t) \Leftrightarrow \epsilon(\omega) = c(\omega)\sigma(\omega),$$

$$\dot{\epsilon}(t) = v(t) \otimes \sigma(t) \Leftrightarrow \omega\epsilon(\omega) = v(\omega)\sigma(\omega)$$

where $c(\omega)$ is the complex compliance and $v(\omega)$ is the complex fluidity.

Figure 1:
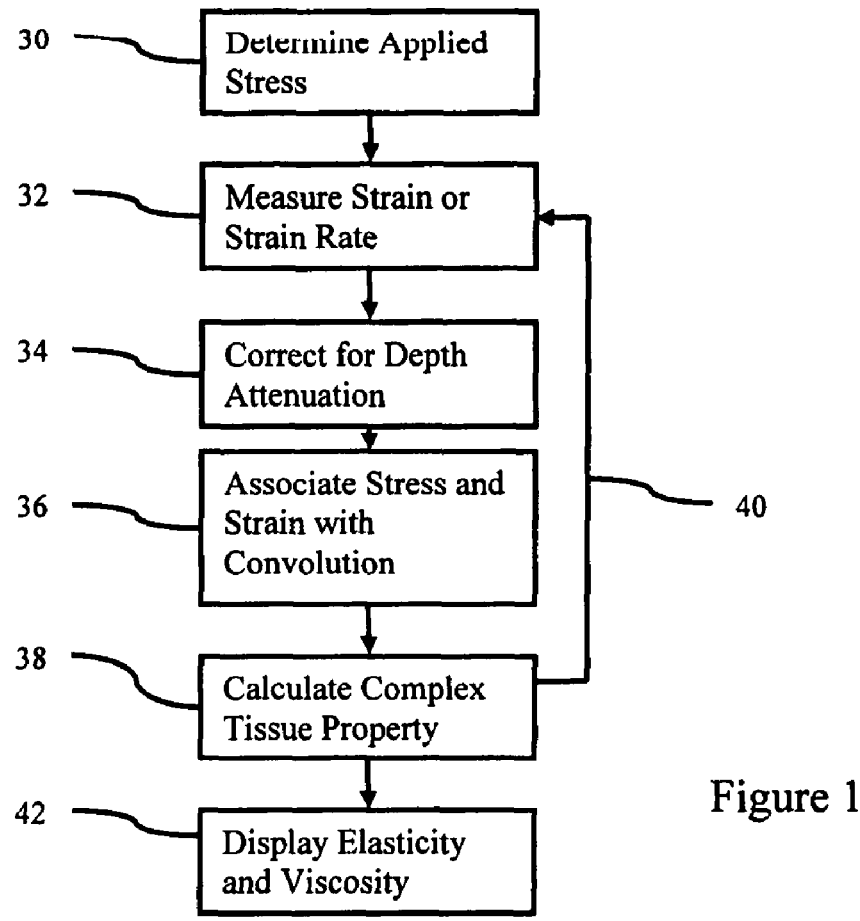
FIG. 1 is a flow chart diagram of one embodiment of a method for determining a viscoelastic tissue property.

FIG. 1 shows a method for determining viscoelastic tissue property. The method is implemented by the system of FIG. 2 or a different system. Additional, different, or fewer acts may be provided. For example, acts 34, 40, and/or 42 are not provided. The acts are performed in the order described or shown, but may be performed in other orders. For example, the depth attenuation correction act 34 is performed as part of or after the convolution of act 36.

In act 30, an applied stress is determined. Compression force, rarefaction force, or other stress is applied to tissue being scanned. For example, a user applies pressure axially with a transducer. Ultrasound scanning is performed while applying pressure with the transducer against the patient. Alternatively, another source of stress or compression is used, such as acoustic energy or a mechanical structure.

The stress may be applied by an external source. External pressure includes acoustic or mechanical pressure. The pressure propagates from outside the patient, such as from a transducer probe, to the tissue or region of interest. The pressure may be generated from within a patient, such as acoustic pressure generated from an intra cavity probe. Acoustic pressure may be a focused or unfocused acoustic radiation force. Mechanical pressure may include a machine (e.g., thumper).

Determining the applied stress may be identifying the type of stress, estimating or measuring the applied stress, or assuming an applied stress. The applied stress is known. The pressure generated by acoustic energy may be measured or calculated once and stored for later use. Alternatively, the known stress is accounted for in the algorithm to determine the tissue property. The determination may be reflected in the process used to determine the complex tissue property. Since the stress or pressure is known, the stress applied may be assumed.

The applied stress may be estimated. For example, a pressure applied manually is measured. As another example, a force applied mechanically or acoustically is measured. In another example, pressure from a source within a patient is estimated. For example, the heart generates pressure within the circulatory system. The pressure within a vessel may be estimated from the velocity profile across the vessel or a velocity at a center of the vessel. Doppler or flow imaging is used to estimate the velocity. The velocity is related to pressure by an empirical or known relationship. The velocity-pressure relationship may be calibrated to an individual patient by measuring static pressure for the patient. As another example, the diaphragm or lungs apply pressure to surrounding tissue during the breathing cycle. The velocity of the tissue is determined by tissue Doppler imaging or tissue tracking. Empirical data or another relationship between the velocity of the diaphragm tissue and pressure is used to estimate the stress.

One method to estimate the stress is to measure the pressure at the body surface with sensors attached to the transducer. The stress field pattern is then extrapolated internally to the points of measured strain.

The applied stress may be impulse, cyclical, repeating, or a non-impulse stress. For example, the pressure applied due to breathing or the heart is cyclical. The stress is applied repetitively, or differently as a function of time.

For cyclical stress, the measurement of act 32 is determined relative to the stress. For example, EKG signals are used to time the measurement of strain relative to the cycle of the stress.

The applied stress may be represented by an impulse. A substantially single pressure wave is generated. The impulse may be generated by a cyclical pulsed waveform of a cycles (e.g., tens or hundreds of cycles). For example, acoustic radiation force is transmitted as an impulse for applying stress to tissue. The impulse wavefront propagates to the region of interest. The amplitude generates the desired level of stress.

In act 32, the tissue strain is measured. The tissue is strained in response to the applied stress. Ultrasound imaging is performed during or just after the stress is applied. Ultrasound data is received in response to transmissions of ultrasound. The transmissions and receptions are performed for a single spatial location, along a line, over an area, or over a volume. A sequence of transmissions and receptions are provided for each spatial location.

The displacement of tissue is determined as a function of time. The displacement may be measured by determining tissue velocity and/or acceleration. The displacement may be measured from tissue data, such as B-mode ultrasound data. Correlation, cross-correlation, minimum sum of absolute differences or other similarity measure is used to determine the displacement between scans. The displacements are determined along one, two, or three dimensions. In one embodiment, any one or more of the methods or systems disclosed in U.S. Pat. Nos. 5,107,837, 5,293,870, 5,178,147, 6,508,768 or 6,558,324, the disclosures of which are incorporated herein by reference, are used to generate elasticity frames of data or images as the strain information.

In act 34, the measured strain is corrected for depth dependent attenuation of the applied stress. As the pressure propagates through tissue, the pressure attenuates. Less motion or displacement is caused at locations spaced further from the source of pressure (depth relative to the source) due to the attenuation. The displacement is adjusted to account for the attenuation, providing more normalized displacements at different spatial locations.

The correction is linear as a function of distance away from the point or region of the source of stress. Non-linear correction may be used, such as based on tissue models or different types of tissue. The linear or non-linear function is assumed, based on empirical data, or is based on a propagation model. For acoustic force, the attenuation of sound in tissue as a function of distance and frequency is corrected. For other external force or force from other organs, such as manually applied force or heart force, no or different correction is provided.

The correction is performed in the time domain. The correction is performed before calculating the strain rate, but may be performed separately for the strain rate. In alternative embodiments, the correction is performed in the Fourier or frequency domain.

In act 36, the applied stress and strain or strain rate are associated as a convolution function. The applied stress and complex compliance or complex fluidity are convolved to provide strain or strain rate. The convolution function allows direct determination of the complex compliance or fluidity, such as represented by:

$$\epsilon(t) = c(t) \otimes \sigma(t) \Leftrightarrow \epsilon(\omega) = c(\omega)\sigma(\omega), \quad \text{equations (1)}$$

$$\dot{\epsilon}(t) = v(t) \otimes \sigma(t) \Leftrightarrow \omega\epsilon(\omega) = v(\omega)\sigma(\omega)$$

By solving for the complex compliance, $c(\omega)$, or the complex fluidity, $v(\omega)$, the tissue may be characterized.

The strain, strain rate, and/or stress are known. The complex compliance or fluidity may be determined based on the convolution function. In one embodiment, the determination is performed in the time domain. In an alternative embodiment, the determination is performed in the frequency or Fourier domain. As shown in the equations (1) above, the convolution in the frequency domain provides an algebraic operation. The tissue strain, such as the strain or strain rate (derivative of strain), are divided by the stress to provide the complex compliance or fluidity, respectively. For complex modulus or viscosity, a multiplication is provided or the reciprocal of the complex compliance or fluidity is determined.

For the convolution function in the frequency domain, the stress or pressure at a given spatial location as a function of time is transformed. A Fourier transform is applied to the stress profile. For an impulse or approximate impulse as the stress, the frequency domain representation is a constant. To avoid unneeded calculations, the stress may not be transformed and the division not performed in recognition of the impulse stress. For an impulse response, the convolution may be provided by merely transforming the strain or strain rate and dividing by a constant.

For non-impulse stress, the stress profile or pressure as a function of time is Fourier transformed. For example, the pressure applied cyclically is transformed. Any transform into the frequency domain may be used.

For directly using the convolution function, the strain and/or strain rate are also Fourier transformed. The tissue strain profile, such as the strain as a function of time or the strain rate as a function of time, is transformed into the frequency domain. The strain rate may be calculated in the time domain or the frequency domain. Any transform into the frequency domain may be used.

In act 38, a complex tissue property is determined based on the convolution function. For example, a complex modulus, complex compliance, complex viscosity, complex fluidity, or combinations thereof are calculated as a function of the tissue displacement and the stress. The complex tissue properties have real and imaginary components. In the time domain, the convolutions of equations (1) are solved for the complex compliance, fluidity, viscosity, or modulus. In the frequency domain, the convolution is provided by division or multiplication.

Only one or multiple complex tissue properties are determined. For diagnosis, both elasticity and viscosity may be desirable. Both complex compliance or modulus and complex fluidity or viscosity are calculated.

The complex representation may be used. Alternatively, further values are determined from the complex tissue property. For example, the elasticity and viscosity are determined. Given a complex compliance, a mean compliance, G, provides the elasticity. Given a complex viscosity, a mean viscosity, η, provides the viscosity. These mean computations are represented by:

$$G = G' + iG'' = \frac{\overline{c}^*(\omega)}{\|\overline{c}(\omega)\|},$$

$$\eta = \eta' + i\eta'' = \frac{\overline{v}^*(\omega)}{\|\overline{v}(\omega)\|}$$

Other values may be determined, such as a standard deviation.

In act 40, the measuring act 32, correction act 34, convolving act 36, and calculating act 38 are repeated for each of a plurality of spatial locations. The measuring act 32 may be performed by scanning, such as scanning a two or three-dimensional region electronically or mechanically with ultrasound. Repetitive scanning acquires data representing the response to the stress from the spatial locations of the scanned region multiple times or as a function of time. The measurements are made from the same data set, but different data representing different spatial locations. The correction act 34 may be applied to the displacements determined for different regions. The repetition of the acts is performed in sequence or parallel with the same of different ultrasound scans.

The complex tissue property or values derived there from are determined for a plurality of spatial locations. Alternatively, no repetition is performed and values are only determined for one spatial location.

In act 42, an image of the tissue property is displayed. The image is modulated or generated as a function of at least one component of the complex tissue property. For example, color, brightness, luminance, hue, or other characteristic is modulated as a function of a real or imaginary portion of the complex tissue property. The component may be mapped linearly or non-linearly to the display values. Other components of the complex tissue property may be used, such as the mean elasticity or viscosity.

More than one tissue property may be displayed in a same image. For example, pixels at one location have color responsive to one component and hue responsive to another component. The display values at different spatial locations may be responsive to different components.

In one embodiment, elasticity and viscosity are displayed at a substantially same time. Substantially accounts for different refresh times. Both components are displayed on a same image, such as each component mapping to display values (e.g., 2D look-up table) or each component mapping to a different display characteristic. Alternatively, both components are mapped to display values for separate representations displayed adjacent to each other on a same screen.

The image provides the complex tissue property for a location, for a line, for an area, or for a volume. For example, a two-dimensional image includes tissue property information for a plurality of spatial locations. As another example, a three-dimensional representation may be rendered, at least in part, from data of one or more components of the complex tissue property.

The image may include other data. For example, B-mode or other data representing tissue, fluid, or contrast agents in the same region is included. The tissue property component is used for an overlay of or combination with the other data.

Figure 3:
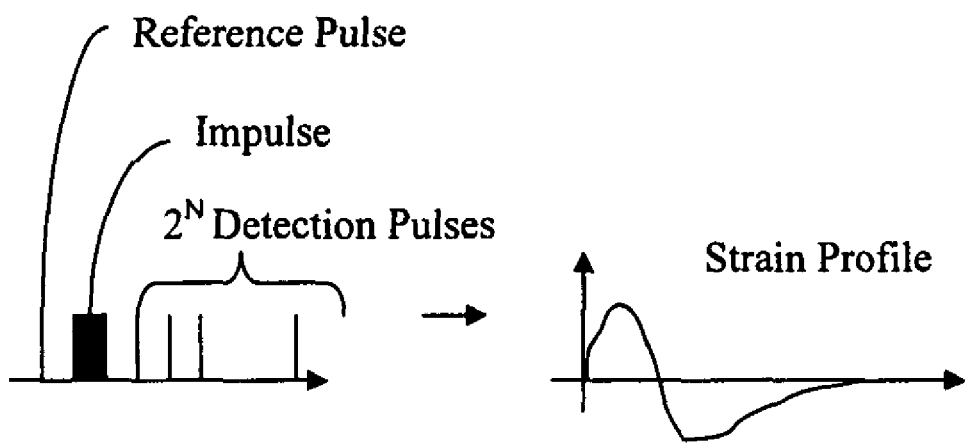
FIG. 3 is a graphical representation of determining strain with an impulse stress.
Figure 4:
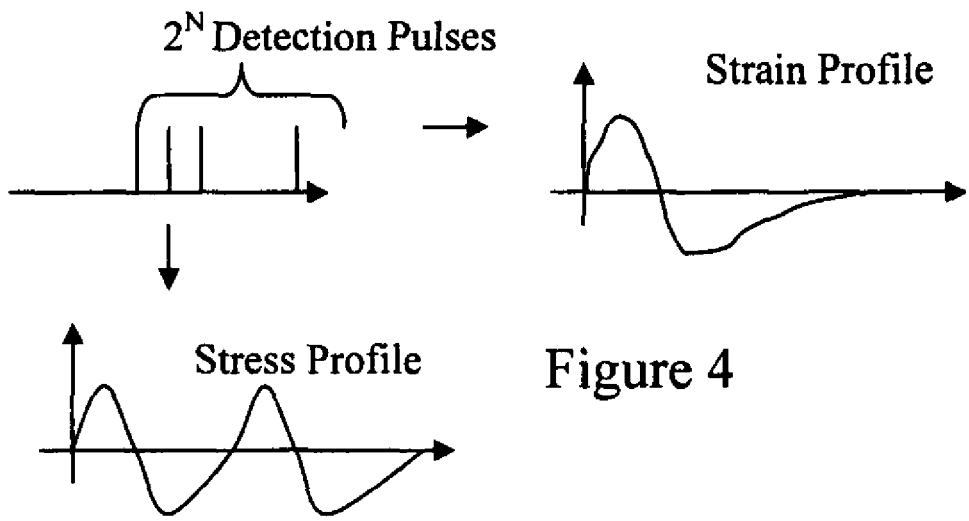
FIG. 4 is a graphical representation of determining strain and stress with a cyclical stress.

FIGS. 3 and 4 show two different embodiments of the method of FIG. 1. FIG. 3 represents the method with an external, impulse stress input. A reference pulse or pulses are used to generate one or more images. The region of interest is identified so that the transducer or scanning region is positioned relative to the tissue of interest. The impulse pressure is generated or occurs. A plurality of scans along one or more scan lines are performed with ultrasound, as represented by the detection pulses. For each spatial location of interest, a strain profile of displacement as a function of time is generated. The displacement may be relative to a first detection after the stress or a reference from before the stress. The strain profile is corrected for depth dependent attenuation of the applied stress. The Fourier transform of the strain profile provides the complex compliance with or without weighting. Since the stress is an impulse, at least by approximation, the convolution is with a value of 1 or other constant in the frequency domain. The derivative of the strain in the time domain provides the strain rate profile. The strain rate is also transformed. The convolution of the strain rate with 1 or other constant in the frequency domain provides the complex viscosity. The elasticity (mean compliance) and viscosity (mean viscosity) are calculated and used for display.

FIG. 4 represents the method with a cyclical, internal stress. The stress is estimated from Doppler velocity estimates. For a cardiac vessel, a remote static pressure may be used to correlate the velocity with a given pressure. For the diaphragm, an empirical relationship of velocity to pressure may be used to determine the pressure. The stress profile of pressure as a function of time is determined. Using the detection pulses, the strain of displacement as a function of time is determined. The temporal relationship of the stress relative to the tissue strain is determined, such as determining the corresponding times from an EKG signal. The derivative of strain may be calculated to provide the strain rate. The Fourier transform of the tissue strain (strain and/or strain rate) and stress profiles are computed. The transform of the strain is divided by the transform of the stress, providing complex compliance. The transform of the strain rate is divided by the transform of the stress, providing complex viscosity. The elasticity (mean of complex compliance) and viscosity (mean of complex viscosity) are calculated and use for display.

Figure 2:
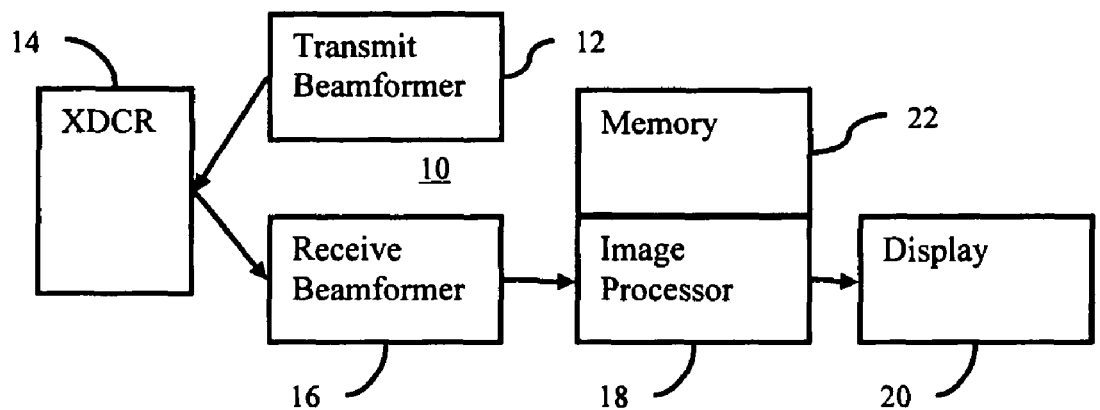
FIG. 2 is a block diagram of one embodiment of a system for determining viscoelastic tissue property.

FIG. 2 shows one embodiment of a system 10 for determining viscoelastic tissue property. The system 10 implements the method of FIG. 1, 2, or 3, or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted selection of display maps, tissue properties to be determined, region of interest selection, or other control. The system 10 is a medical diagnostic ultrasound imaging system. In alternative embodiments, the system 10 is a personal computer, workstation, PACS station or other arrangement at a same location or distributed over a network for real-time or post acquisition imaging, so may not include the beamformers 12, 16 and transducer 14.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed. A sequence of transmit beams are generated to scan a two or three-dimensional region. Sector, Vector®, linear or other scan formats may be used. The same region is scanned multiple times. For flow or Doppler imaging and for strain imaging, a sequence of scans are used. In Doppler imaging, the sequence may include multiple beams along a same scan line before scanning an adjacent scan line. For strain imaging, scan or frame interleaving may be used (i.e., scan the entire region before scanning again). In alternative embodiments, the transmit beamformer 12 generates a plane wave or diverging wave for more rapid scanning.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer. The elements connect with channels of the transmit and receive beamformers 12, 16.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for Doppler or flow data.

The image processor 18 is a B-mode detector, Doppler detector, pulsed wave Doppler detector, correlation processor, Fourier transform processor, application specific integrated circuit, general processor, control processor, field programmable gate array, digital signal processor, analog circuit, digital circuit, combinations thereof or other now known or later developed device for detecting and processing information for display from beamformed ultrasound samples.

In one embodiment, the image processor 18 includes one or more detectors and a separate processor. The processor is a control processor, general processor, digital signal processor, application specific integrated circuit, field programmable gate array, network, server, group of processors, data path, combinations thereof or other now known or later developed device for determining strain, performing Fourier transforms, and calculating complex tissue property components. For example, the processor 18 performs any combination of one or more of the acts shown in FIG. 1.

In one embodiment, the image processor 18 determines strain and/or strain rate as a function of the output data from the receive beamformer 16. The processor 18 may also determine a stress profile. The strain, strain rate, and/or stress are transformed into the frequency domain. Elasticity and viscosity tissue properties are calculated by algebraic function in the frequency domain, such as dividing the transformed strain or strain rate by a transform of a stress applied to tissue. The image processor 18 outputs image or display values mapped from the tissue properties to the display 20.

For determining strain, strain rate, and/or stress, data from a plurality of scans or measurements is acquired and stored. The data is stored in the memory 22 or a different memory. Data from one or more stages of processing is stored, such as radio frequency data, channel data, beam sum data, detected data, strain data, strain rate data, stress data, transformed data, and/or calculated complex tissue property components.

The image processor 18 operates pursuant to instructions stored in the memory 22 or another memory. The processor 18 is programmed for determining viscoelastic tissue property. The memory 22 is a computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 displays ultrasound images, complex tissue property values, and/or images representing complex tissue property components, such as images for elasticity and viscosity tissue properties for a plurality of spatial locations.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for determining viscoelastic tissue property, the method comprising:
    determining an applied stress, the determining the applied stress comprises identifying an impulse function representing the applied stress;
    measuring, with ultrasound, tissue strain in response to the applied stress; and
    determining, with a processor, a complex tissue property as a convolution function of the impulse function of the applied stress and the tissue strain, the impulse function and the tissue strain being variables in the convolution function.

2. The method of claim 1 wherein determining the complex tissue property comprises Fourier transforming the tissue strain where a Fourier domain representation of the impulse is a constant.

3. The method of claim 1 wherein measuring comprises determining displacement as a function of time from received ultrasound signals.

4. The method of claim 1 wherein determining the complex tissue property comprises dividing in a Fourier domain.

5. The method of claim 1 wherein determining the complex tissue property comprises determining the elasticity and the viscosity.

6. The method of claim 1 further comprising:
    repeating measuring, and determining the complex tissue property for each of a plurality of spatial locations; and
    displaying an image of at least one component of the complex tissue property, the image representing at least the plurality of spatial locations.

7. The method of claim 1 further comprising:
    correcting for depth dependent attenuation of the applied stress.

8. A method for determining viscoelastic tissue property, the method comprising:
    determining an applied stress, wherein determining the applied stress comprises estimating cyclic pressure;
    measuring, with ultrasound, tissue strain in response to the applied stress; and
    determining, with a processor, a complex tissue property as a convolution function of variation of the cyclic pressure and tissue strain.

9. The method of claim 8 wherein determining the complex tissue property comprises:
    Fourier transforming the cyclic pressure and the tissue strain; and
    dividing the transformed tissue strain by the transformed cyclic pressure.

10. A system for determining viscoelastic tissue property, the system comprising:
    a transducer operable to generate receive signals from received ultrasound energy;
    a receive beamformer operable to output data representing spatial locations along at least a line;
    an image processor operable to determine strain or strain rate as a function of the output data, operable to transform the strain or strain rate into a frequency domain, and operable to calculate elasticity and viscosity tissue properties by algebraic function in the frequency domain, the calculation including a constant based on an impulse function representing acoustic radiation force applied to tissue, the strain or strain rate responsive to the acoustic radiation force.

11. The system of claim 10 further comprising:
    a display operable to display elasticity and viscosity tissue properties for a plurality of spatial locations in one or more images.

12. The system of claim 10 wherein the image processor is operable to calculate by dividing the transformed strain or strain rate by a transform of a stress applied to tissue.

* * * * *